United States Patent [19]

Avera

[11] Patent Number: 4,865,640

[45] Date of Patent: Sep. 12, 1989

[54] MOISTURIZING AGENT

[76] Inventor: F. Lee Avera, 1809 Yale Dr., Alameda, Calif. 94501

[21] Appl. No.: 279,030

[22] Filed: Dec. 2, 1988

Related U.S. Application Data

[63] Continuation-in-part of Ser. No. 910,676, Sep. 23, 1986, abandoned.

[51] Int. Cl.$^4$ ............................................. C05F 11/00
[52] U.S. Cl. .......................................... 71/23; 71/26; 71/903; 536/98; 47/9
[58] Field of Search ............................ 71/23, 26, 903; 524/561; 536/98; 424/445; 47/9

[56] References Cited

U.S. PATENT DOCUMENTS

| | | | |
|---|---|---|---|
| 3,287,222 | 11/1966 | Larde et al. | 424/445 |
| 3,337,326 | 8/1967 | Nadler | 71/23 X |
| 4,090,022 | 5/1978 | Tsao et al. | 536/98 |
| 4,102,842 | 7/1978 | Fujimoto et al. | 524/561 |

*Primary Examiner*—Ferris H. Lander
*Attorney, Agent, or Firm*—Bielen & Peterson

[57] ABSTRACT

A moisturizing substrate for plant and animal tissue utilizing a mixture of cellulosic compound with carboxylic groups substituted on glucose units of cellulosic chain through an ether linkage. The cellulosic compound is admixed with a hydrated metallic salt and aerated water. The substrate may be mixed with soil or used in a layered relationship with a soil.

8 Claims, No Drawings

MOISTURIZING AGENT

The present application is a continuation-in-part of pending application Ser. No: 910,676, Filed: 23 Sept. 1986 and now abandoned.

BACKGROUND OF THE INVENTION

The present invention relates to a novel and useful substrate which may be used as a moisturizing agent for plant and animal tissue. It is often a problem to maintain the moisture content of soils to a level which would sustain the viability of a plant growing within the soil. In the past, moisture is typically added to the soil by watering using manual or automatic means, such as sprinkler systems. Prior growth substrates have resembled sponge like materials which require the addition of water during highly evaporative conditions e.g. hot weather, high winds, and the like. The prior art substrates have been subject to evaporation and require more frequent watering in adverse condition.

Cut flowers seldom survive long periods of hot weather exposure even when watered by wet, sponge-like materials. It is impractical to transport cut flowers long distances without soaking the cut flowers in a water container. This is a prohibitively expensive method of transporting of cut flowers. The same problem occurs with the transportation of seedling trees used for reforestation projects.

Certain medical conditions require the application of water. Treatment of burns, for example, entail soaking the burnt tissue in water or constantly adding water to a gauze or sponge-like bandage. The provision of moisture in this way is often ill timed since a great deal of labor is required to maintain the moisture level of a burn treatment bandage.

A moisturizing agent which gradually releases water to plant or animal tissue and is not subject to excessive evaporation would be a great advance in the agricultural, medical and cosmetic fields.

SUMMARY OF THE INVENTION

In accordance with the present invention a novel and useful moisturing substrate is provided.

The moisturizing substrate of the present invention takes the form of a high viscosity substance which gradually releases water and air when interacting with biological organisms present in the environment of the object receiving the water and air. Although the mechanism of release of water and air is not clearly understood, it is believed that micro-biological organisms such as enzymes, fungi, and/or ferments, are responsible for the time release for water and air of the substrate.

The high viscosity of substrate may be formed by using a basic cellulosic substance, such as natural bark, which may include glucose, units on its molecular cellulosic chain. A cellulosic compound is formed by substituting carboxylic groups on the glucose units of the cellulosic chain through an ether linkage. More specifically, the cellulosic compound may have the formula:

in which "M" is a metal substituted for hydrogen on said carboxyl group of the cellulosic compound, and "R" is a cellulosic chain. "M" may be represented by lithium, sodium, potassium, rubidium and/or cesium. The cellulosic compound shown in the above formula has a very high average molecular weight, on the ranging from 90,000 to 700,00.

The cellulosic compound, above described, is mixed with a hydrated metallic salt. For example, aluminum sulfate having 18 molecules of water mechanically held to a single aluminum sulfate molecule will suffice in this regard. Zinc sulfate indium sulfate, cadmium sulfate and gallium sulfate may also be used in their hydrated forms in substitution for hydrated aluminum sulfate. The cellulosic compound and hydrated metallic salt is vigorously mixed with aerated water. The resultant substrate is a jelly-like substance of very high viscosity having entrained air bubbles.

The present invention may also be deemed to encompass a method of providing water and gas to plant organisms, such as flowers, shrubs, trees and the like, by mixing a 40-60% by weight quantity of a substrate, described above, with soil. The admixture of the substrate and soil is placed in contact with the plant, preferably in a container. Water and gas held by the substrate will gradually be fed to the plant over a selected time period. Water may be replenished to the substrate by adding the same to the substrate soil mixture after depletion of the water by the plant.

Another method within the purview of the present invention requires placing the substrate described above on the top surface of the soil in a potted plant. Again, water may be replenished to the substrate after depletion of the same by the potted plant.

A further method of the present invention involves the use of the substrate above described on animal tissue where water is required such as in the treatment of a burn. In this case the substrate is placed adjacent to the burnt area of skin and held in place by a bandage for a selected time period.

It may be apparent that a novel and useful substrate and method for employment of the same as a moisturizing agent has been described.

It is therefore an object of the present invention to provide a moisturizing substrate which is easily manufactured and gradually releases water and gas to animal and plant tissue.

It is another object of the present invention to provide a moisturizing substrate which is highly resistant to evaporation at high atmospheric temperatures.

Another object of the present invention is to provide a moisturizing substrate for animal and plant tissue.

It is yet another object of the present invention to provide a moisturizing substrate which is insoluble in water, and has moisture releasing capability which may be regenerated by the addition of water.

Another object of the present invention is to provide a moisturizing substrate which may be easily stored for long periods of time and used for its intended purpose thereafter.

Yet another object of the present invention is to provide a moisturizing substrate which may be employed with potting soil to release moisture and gas to a plant in contact with the potting soil.

Another object of the present invention is to provide a moisturizing substrate which is capable of preserving cut flowers permitting them to be transported long distances without wilting.

A further object of the present invention is to provide a moisturizing agent which is usable in certain medical procedures requiring moisturization such as the treatment of burns, dental dry sockets and the like.

Yet another object of the present invention is to provide a moisturizing substrate which does not flow under gravity.

A further object of the present invention is to provide a moisturizing substrate which is sterilized at boiling water temperature but does not deteriorate under boiling water temperature.

A further object of the present invention is to provide a moisturizing substrate which may be used cosmetically on human skin.

The invention may be illustrated by the following examples but is not deemed to be limited by the same.

EXAMPLE I

Water (97.8 parts per 100) at room temperature was vigorously agitated to quickly become saturated with air. A mixture of powders (2.1 parts per 100) comprising high viscosity type R—O—COONa (2.1 parts per 100) and aluminum sulfate hydrate Al $(SO4).18H0$ (0.1 parts per 100) were slowly added to the air saturated water under high intensity mixing conditions. The R—O—COONa component of this mixture consisted of R as a cellulosic compound, originally having at least one glucose unit, with a molecular weight on the order of 700,000 and where the carboxylic group is substituted on the glucose unit of the cellulosic chain through an ether linkage. The mixing resulted in a viscous substrate formed of a water solution of the powder solids and also contained entrained air bubbles. The still gravity flowable, but viscous, mixture was transferred to a container and allowed to set for a short period of time. The gravitation flowability decreased while setting. The jelly-like product then appeared dry to the touch but semi-sold in appearance. It was found that the aerated water portion of the substrate may vary plus or minus 0.5 parts, the R—O—COONa powder portion of the mixture may vary plus or minus 0.4 parts and the hydrated aluminum sulfate portion of the mixture may vary 0.01 parts, without substantially altering the substrate properties. The substrate produced was observed to not melt or deteriorate in boiling water after 30 minutes of boiling the substrate in a container placed in the boiling water. The substrate was insoluble in water. Evaporation at 100° F. in ambient atmospheric conditions was strongly resisted by the substrate produced. The substrate was determined by calculation to be approximately 98% water. The elemental structure was determined to be 0.76% carbon, 10.95% hydrogen, 88.00% oxygen, 0.008% aluminum 0.286% sodium and 0.10% sulfur. The substrate formation was repeated with the addition of inert green food coloring without affecting the moisturizing characterics of the substrate.

EXAMPLE II

The substrate of Example I was employed with a freshly cut flower (Rainbow Astor). The stem of a freshly cut flower was immersed in water for (30) minutes. The stem was then removed from the water, drained, and briefly squashed, to promote the flow of stem juices. A very thin coating of the substrate was placed around the lowest one-half inch of the stem and enclosed in aluminum foil. It was observed that the flower remained unwilted for (1) week. The substrate decreased in volume during that time period. Another cut flower (Rainbow Astor) similarly prepared, without contacting the substrate of Example 1, wilted after one week.

EXAMPLE III

The substrate of Example I was admixed in equal parts with potting soil. A small marigold plant was placed in a pot containing the admixture as a base. The plant survived for two weeks without watering. The admixture diminished to about one-half its original volume during this period of time. Damp potting soil was added to replenish the missing volume and the plant continued to survive for about (2) additional weeks without watering. A control marigold plant placed in wet potting soil without the substrate of Example 1, did not survive after (2) weeks.

EXAMPLE IV

A small potted marigold plant was placed in a pot containing about 2 inches of potting soil. A layer of the substrate of Example I averaging one inch in thickness was placed on top of the potting soil to cover about one-half of the upper surface of the potting soil. The plant survived for about two weeks without further nourishment.

EXAMPLE V

A quarter to half inch layer of the substrate of Example I was placed on top of 2 inches of dry potting soil. Grass seed was sprinkled on the top of the substrate and covered with a thin layer of potting soil. After one week healthy grass sprouts were germinated and continued to grow for another week without watering. After the initial two week period the grass was watered for a short time. Then watering took place every two weeks for a short period. The grass sprouts matured into healthy grass plants and flourished under this water schedule.

EXAMPLE VI

The substrate of Example I was placed on a chemical skin burn on a patient's arm. The patient reported that the substrate reduced the pain of the burn and healing of the burn proceeded at a rapid rate.

EXAMPLE VII

Water (97.1% parts per 100) at room temperature was saturated with air. a mixture of powders consisting of 0.1% aluminum sulfate hydrate (Al2 $(SO4)_3 .18H20$ and 2.0% cellulosic gum having a average molecular weight of 90,000 and 7.0–8.99% by weight sodium substituted, of the type R—O—COONa, were slowly added to the air saturated water under high intensity mixing conditions. The cellulosic gum, also known as Sodium Carboxymethylcellulose (CMC), possessed a viscosity at 2% by weight in water centipoise of 25–50(cp). The resultant substrate product included a gel portion releasably carrying water and air, but was soft and wet to the touch.

EXAMPLE VIII

Water (97.1% parts per 100) at room temperature was saturated with air. A powder mixture consisting of 0.1% by weight Al2 $(SO4)_3 .18H20$ and 2.8% w/w C.M.C. was mixed into the air saturated water as in Example VII. The resultant substrate contained releasable water and air and exhibited excellent gel properties (being dry to the touch).

EXAMPLE IX

Air saturated water was prepared as in Example VII. A mixture of powders consisting of 0.1% by weight Al$_2$(SO4)$_3$.18H20 and 2.8%, by weight CMC having a average molecular weight of 250,000, 8.1 to 9.2% by weight sodium substituted, and a viscosity of about 3100(cp) at 2% by weight in water, was added to the air saturated water as in Example VII. A second mixture of powders consisting of the same aluminum sulfate hydrate portion, 2.0% by weight CMC, and 97.9% by weight air saturated water (prepared as in Example VII). Both preparations resulted in a gel containing releasable air and water, the higher CMC content substrate having an excellent (dry to the touch) gel structure; the lower CMC substrate having a good gel structure.

EXAMPLE X

A powdered CMC compound having a average molecular weight of 250,000, being 7.0-8.9% w/w sodium substituted, and possessing viscosity at 2% by weight in water of 800 cp was mixed in 2.0% weight proportion with 0.1% weight proportion of Al$_2$ (SO4)$_3$ .18H20. This powder mixture was added 97.9% by weight of air saturated water, prepared per Example VII. The resultant substrate contained releasable water and air, but was soft and wet to the touch.

EXAMPLE XI

The components of Example X were mixed in the following proportions:
98% by weight water
0.1% by weight Al$_2$ (SO4)$_3$ .18H20, and
1.9% by weight CMC
according to the process defined in Example VII. The substrate product resulted in a substrate containing releasable water and air having a good gel structure.

EXAMPLE XII

A substrate prepared according to Example I was packed in a number of transparent containers and sealed with closure caps. The containers were shaped such that the end closed with a cap was larger than the opposite end. Each container was opened, inverted and placed on the soil surface of a potted plant. The substrate gel slowly disappeared, delivering air and water to the plants in the process. The transparent container served as a gauge for the mass of gel remaining and prevented evaporation of water in the gel to the ambient atmosphere. The following table represents the observed substrate life with respect to various pots and plants:

| POT SIZE (inches in dia.) | PLANT SIZE | SUBSTRATE WEIGHT (ounces) | NUMBER OF INVERTED CONTAINER | SUBSTRATE LIFE |
| --- | --- | --- | --- | --- |
| 6-7 | Medium | 5½ | 1 | 25 |
| 8-9 | Medium | 3½ | 2 | 21 |
| 8-9 | Large | 5½ | 2 | 25 |
| 10-11 | Large | 7 | 2 | 30 |
| 12-16 | Large | 9 | 2 | 30 |

EXAMPLE XIII

A dozen redwood and ponderosa pine tree clones, normally employed in reforestation projects, were stored for several days in wet newspapers and were observed to be in a wilted condition at the end of this period. Each tree was assigned a one gallon plastic pot. In each pot was placed a 50%/50% volemutric mixture of redwood mulch and top soil, and a small amount of chicken manure. Three ounces of substrate prepared according to Example I was placed in the center of each pot. Each tree was suspended above the substrate and the top soil/mulch mixture was added to surround the roots and fill the pot. Each pot was then watered and lightly tapped. The pots were placed in an outdoor shaded area for one month during hot summer weather in Guerneville California. The top soil/mulch upper surface of each pot became quite dry, yet each tree exhibited excellent growth and nurture. After the month period, selected pots were opened. The soil in the root area was moist and cool surrounding the root area of the tree, although no water had been added to the pots during the month preceding opening of the pots.

While in the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A substrate which gradually releases impregnated water and gas when interacting with a biological organism essentially comprising a mixture of:
   a. cellulosic compound ranging from 13% by weight having an average molecular weight ranging between 90,000 and 700,000 represented by the formula:
   R—O—COOM, in which "M" is a metal substituted for hydrogen on said carboxyl group of the cellulosic compound and "R" is cellulosic chain;
   b. a hydrated metallic salt ranging from 0.1-0.3% by weight; and
   c. water ranging from 97-99% by weight.

2. The high viscosity substrate of claim 1 in which said water is aerated.

3. The substrate of claim 1 in which said metal of said cellulosic compound is selected from the group essentially comprising:
   lithium, sodium, potassium, rubidium and cesium.

4. The substrate of claim 1 in which said hydrated metallic salt is selected from the salt group essentially comprising:
   aluminum sulfate, zinc sulfate, indium sulfate, cadmium sulfate and gallium sulfate with water being held mechanically to the salt molecule.

5. A method of providing water and gas to a plant organism comprising:
   a. mixing a 40-60% quantity by weight of a substrate comprising a mixture of a cellulosic compound ranging from 1-3% by weight including glucose units and having an average molecular weight ranging between 90,000 and 700,000 represented by the group;

R—O—COOM, where "M" is a metal substituted on said glucose units of the cellulosic compound and "R" is a cellulosic chain;

a hydrated metallic salt ranging from 0.1–0.3% by weight aerated water; and ranging from 9.7–9.9% by weight a. 40–60% quantity by weight of soil
b. placing said admixture in contact with the plant.

6. A method of providing water to a plant organism comprising:
  a. placing soil in contact with the plant;
  b. placing a substrate on the top surface of said soil, said substrate essentially comprising a mixture of:
    a cellulosic compound ranging from 0.1–0.3% by weight including glucose units and having a molecular weight ranging between 90,000 and 700,000 represented by the group:
    R—O—COOM, where "M" is a metal substituted on said glucose units of the cellulosic compound and "R" is a cellulosic chain;
    a hydrated metallic salt ranging from 1–3% by weight; and
    aerated water ranging from 97–99% by weight 7. A method of providing water to a young tree in soil comprising:
  a. placing a substrate in the soil, said substrate essentially comprising a mixture of:
    a cellulosic compound ranging from 1–3% by weight including glucose units and having a molecular weight ranging between 90,000 and 700,000 represented by the group:
    R—O—COOM, where "M" is a metal substituted on said glucose units of the cellulosic compound and "R" is a cellulosic chain; a hydrated metallic salt ranging from 0.1–0.3% by weight; and
    aerated water; and ranging from 97–99% by weight
  b. placing young tree roots in the vicinity of the substrate.

8. The method of claim 7 which additionally comprises the step of:
  adding soil to cover the root area of the young tree after said step of placing young tree roots in the vicinity of the substrate.

* * * * *

UNITED STATES PATENT OFFICE
CERTIFICATE OF CORRECTION

Patent No. 4,865,640              Dated 12 September 1989

Inventor(s)   F. LEE AVERA

It is certified that error appears in the above-identified patent and that said Letters Patent is hereby corrected as shown below:

IN THE CLAIMS:
Col. 6,
Claim 1, line 4; change "13%" to --1-3%--.
Col. 7,
Claim 5, line 13; delete ";and".

Col. 7, claim 5, line 8, change "9.7%-9.9%" to --97-99%--.
Col. 7,
Claim 5, line 14; add --;and-- after "weight".
Col. 7,
Claim 5, line 15; delete "a.".

Col. 7, claim 6, line 6, change "0.1-0.3%" to --1-3%--.
Col. 8,
Claim 6, line 13; change "1-3%" to 0.1-0.3%--.
Col. 8,
Claim 7, line 13; delete ";and" after "aerated water".

Signed and Sealed this

First Day of June, 1993

Attest:

MICHAEL K. KIRK

Attesting Officer     Acting Commissioner of Patents and Trademarks